(12) United States Patent
Assmann

(10) Patent No.: US 8,428,325 B2
(45) Date of Patent: Apr. 23, 2013

(54) METHOD FOR PERFORMING AN IMAGING EXAMINATION TECHNIQUE

(75) Inventor: Stefan Assmann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 970 days.

(21) Appl. No.: 12/457,912

(22) Filed: Jun. 25, 2009

(65) Prior Publication Data

US 2009/0324038 A1  Dec. 31, 2009

(30) Foreign Application Priority Data

Jun. 30, 2008  (DE) .......................... 10 2008 030 890

(51) Int. Cl.
*G06K 9/00* (2006.01)

(52) U.S. Cl.
USPC ............................. 382/131; 382/130; 600/407

(58) Field of Classification Search .................. 382/130, 382/131; 600/407
See application file for complete search history.

(56) References Cited

U.S. PATENT DOCUMENTS

| | | | | |
|---|---|---|---|---|
| 6,464,641 B1* | 10/2002 | Pan et al. | ...................... | 600/453 |
| 7,043,290 B2* | 5/2006 | Young et al. | ................... | 600/416 |
| 2006/0159322 A1 | 7/2006 | Rinck et al. | | |
| 2006/0173279 A1 | 8/2006 | Assmann | | |
| 2007/0038058 A1* | 2/2007 | West et al. | .................... | 600/407 |
| 2007/0081712 A1* | 4/2007 | Huang et al. | ................... | 382/128 |

FOREIGN PATENT DOCUMENTS

| | | |
|---|---|---|
| DE | 102004043677 A1 | 3/2006 |
| DE | 102004059133 A1 | 7/2006 |

* cited by examiner

*Primary Examiner* — Claire X Wang
*Assistant Examiner* — Katrina Fujita
(74) *Attorney, Agent, or Firm* — Harness, Dickey & Pierce, PLC

(57) ABSTRACT

A method is disclosed for performing an imaging examination technique. In at least one embodiment, the method includes measuring a first dataset via a first imaging examination technique, measuring a second dataset via a second imaging examination technique, segmenting the first dataset, transferring the segmentation to the second dataset, selecting at least one localization in the second dataset on the basis of the transferred segmentation, and measuring a third dataset via a third imaging examination technique such that the third dataset includes the at least one localization.

22 Claims, 3 Drawing Sheets

METHOD FOR PERFORMING AN IMAGING EXAMINATION TECHNIQUE

PRIORITY STATEMENT

The present application hereby claims priority under 35 U.S.C. §119 on German patent application number DE 10 2008 030 890.0 filed Jun. 30, 2008, the entire contents of which are hereby incorporated herein by reference.

FIELD

At least one embodiment of the present invention generally relates to a method for performing an imaging examination technique.

BACKGROUND

Imaging examination methods enable a physician or radiologist to diagnose a multiplicity of patient diseases. Many diseases require special examination techniques in order to ensure a reliable diagnosis. In particular in the treatment of vascular diseases, but also in tumor treatment, imaging diagnostics is becoming increasingly important. In the diagnosis and treatment of arteriosclerosis, for example, it is desirable to be able to quantify the plaques occurring in a patient's vascular system and leading to arteriosclerosis. Treatment is possible for example by means of diet or the use of cholesterol-lowering medicines. Until now it has only been possible to monitor individual plaques and their variation over time.

Positron emission tomography (PET) is becoming increasingly widely established alongside magnetic resonance tomography (MR) in medical diagnostics. While MR is an imaging method for representing structures and slices inside the body, PET allows in vivo visualization and quantification of metabolic activities.

PET uses the special properties of positron emitters and positron annihilation in order to quantitatively determine the function of organs or cell regions. With this technique, appropriate radiopharmaceuticals marked with radionuclides are administered to the patient prior to the examination. As they decay, the radionuclides emit positrons which after a short distance interact with an electron, causing what is termed annihilation to occur. This results in two gamma quanta which fly apart in opposite directions (offset by 180°). The gamma quanta are detected by two opposing PET detector modules within a specific time window (coincidence measurement), as a result of which the annihilation site is localized to a position on the line connecting said two detector modules.

In the case of PET, the detector module must generally cover a greater part of the gantry arc length for the purpose of detection. It is subdivided into detector elements having a side length of a few millimeters. On detecting a gamma quantum, each detector element generates an event record that specifies the time and the detection location, i.e. the corresponding detector element. This information is passed to a fast logic unit and compared. If two events coincide within a maximum time interval, it is assumed that a gamma decay process is taking place on the connecting line between the two associated detector elements. The PET image is reconstructed using a tomography algorithm, i.e. so-called back-projection.

Recorded PET images can be used for diagnosing plaques. According to a known method, PET images of a bodily region are recorded for that purpose using the tracer $^{18}$F fluorodeoxyglucose (FDG) and sites with increased metabolism, so-called "hot spots", are identified. Because plaques or, as the case may be, inflamed vascular walls are characterized by increased metabolism, they become visible in this way in the recorded PET image. However, there are other phenomena, such as tumors, for example, which can also lead to an increased metabolism and therefore are likewise visible in the recorded PET image.

On the basis of the recorded PET image it is therefore hardly possible to decide which hot spots belong to a vascular wall, that is to say to a plaque, and which are attributable to other diseases. In order to support the interpretation of the recorded PET images, in many cases CT images of the same region are recorded in which calcifications, commonly referred to as "hard" plaques, are represented. If the calcifications coincide with a hot spot from the recorded PET image, the increased metabolism can easily be attributed anatomically with the aid of the recorded CT image. That said, however, it is only in a small number of cases that calcifications occur simultaneously with inflammations at the same point of the vascular wall, so assigning the hot spots to vascular walls is possible only in a few instances.

Furthermore, with known methods the assignment must be carried out manually, which process is both error-prone and time-consuming. In addition, the composition of so-called "soft" plaques cannot be determined by means of CT analyses. Soft plaques can be, for example, fat deposits, thrombi, connective tissue or tissue capsules. Nowadays, said types of soft plaques are readily distinguishable using established magnetic resonance tomography methods. Typing soft plaques is essential for the diagnosis, since it is precisely these soft plaques which are generally vulnerable and can lead to infarctions or embolisms.

SUMMARY

In at least one embodiment of the present invention, a method is disclosed for performing an imaging examination technique by which specific localizations in a patient's body can be efficiently investigated.

According to an example embodiment variant of the invention, a method for performing an imaging examination technique is disclosed, comprising the following:

Measure a first dataset by means of a first imaging examination technique,
measure a second dataset by means of a second imaging examination technique,
segment the first dataset,
transfer the segmentation to the second dataset,
select at least one localization in the second dataset on the basis of the transferred segmentation, and
measure a third dataset by means of a third imaging examination technique such that the third dataset includes the at least one localization.

By using the first and second dataset, it is for example possible to represent anatomical details of a patient in the first dataset, while the second dataset is optimized specifically for an actually present or suspected lesion or medical condition. The segmentation of the first dataset is intended to ensure, for example, that only desired regions or anatomical details of the dataset are taken into account. By transferring the segmentation to the second dataset it is also possible there to restrict the data quantities to the lesions or disease patterns present.

Furthermore, the transferred segmentation can be used as a basis for conducting a targeted search for the localization of a disease and identifying same. In order to allow more precise specification of the data present in the second dataset, a further examination is performed within which a third dataset is created by which the disease or lesion found at the localization can be examined in greater detail. The third dataset can be recorded in particular on the basis of the selected localization, i.e. imaging parameters that control the medical imaging device by which the third dataset is recorded are determined based on the selected localization, etc . . .

Simply by transferring the segmentation from the first to the second dataset it is possible to narrow down the amount of data in the second dataset in such a way that a diagnosis by a physician will subsequently be possible. The physician's diagnostic activity can be further facilitated and improved by measurement of the third dataset at the localization.

In an advantageous embodiment of the method, the first and second imaging examination techniques are performed on isocentric target volumes, the segmentation being transferred isocentrically between the first and second dataset. In the specified constellation, the target volumes of the two imaging examination techniques have the same center points. The modality-related geometry simplifies the transfer of the segmentation, since the datasets can be superimposed isocentrically on one another in any case. This is the case, for example, with fully integrated modalities, or when the first and second imaging examination techniques are performed using the same modality, using different measurement parameters, for example.

One embodiment of the method is advantageous in that the target volumes of the first and second imaging examination technique have isocenters at different locations and the segmentation is transferred between the first and second dataset following a translation of the segmentation which is embodied in such a way that, by way of it, the two isocenters can be transferred into each other. In the case of target volumes having different isocenters it is first necessary to translate the segmentation so that the two datasets start from the same coordinate origin.

In an advantageous embodiment of the invention, the selection of the at least one localization comprises the following:
  Identify regions of interest in the second dataset,
  compare the location of the regions of interest with the segmentation,
  identify at least one of the regions of interest that satisfies a predetermined location criterion within the segmentation, and
  specify the at least one localization as the center of the at least one identified region of interest.

By identifying regions of interest (or points) in the second dataset and comparing the location of the regions of interest with the segmentation it is possible to identify those regions of interest which satisfy a predetermined location criterion within the segmentation. This can be, for example, the association with a further region of interest identified within the segmentation. The localization is then placed into the thus identified regions of interest for the purpose of the following measurement of the third dataset. The regions of interest can be identified by way of a threshold value comparison, for example.

In an advantageous embodiment of the method, the at least one localization is visualized on a display medium together with the first dataset and a user is given the option to select one or more localizations for further investigation. In the case of extensive examinations in particular, this offers the possibility of selecting preferred localizations in a simple manner.

One embodiment of the invention is advantageous in that at least one vessel is isolated by way of the segmentation. This is important in particular for the diagnosis of plaques, since the association with a vessel is easily identifiable by means of the segmentation.

In an advantageous embodiment of the invention, the segmentation comprises the following:
  Calculate a central line through the center of the vessel and specify at least one region around the central line in such a way that the region contains the vessel.

This is a particularly simple method for isolating a vessel. The region around the central line is preferably a tube, the diameter of the tube being greater than the maximum vessel diameter. In this way it can be ensured even if the co-registration of the first and second dataset is not exact that all lesions located in the vascular wall and all disease patterns are recorded. Possible inaccuracies in the segmentation can likewise be compensated.

BRIEF DESCRIPTION OF THE DRAWINGS

Further advantages and embodiments of the invention will emerge from the example embodiments described below in conjunction with the figures, in which.

DETAILED DESCRIPTION OF THE EXAMPLE EMBODIMENTS

Figure 1:
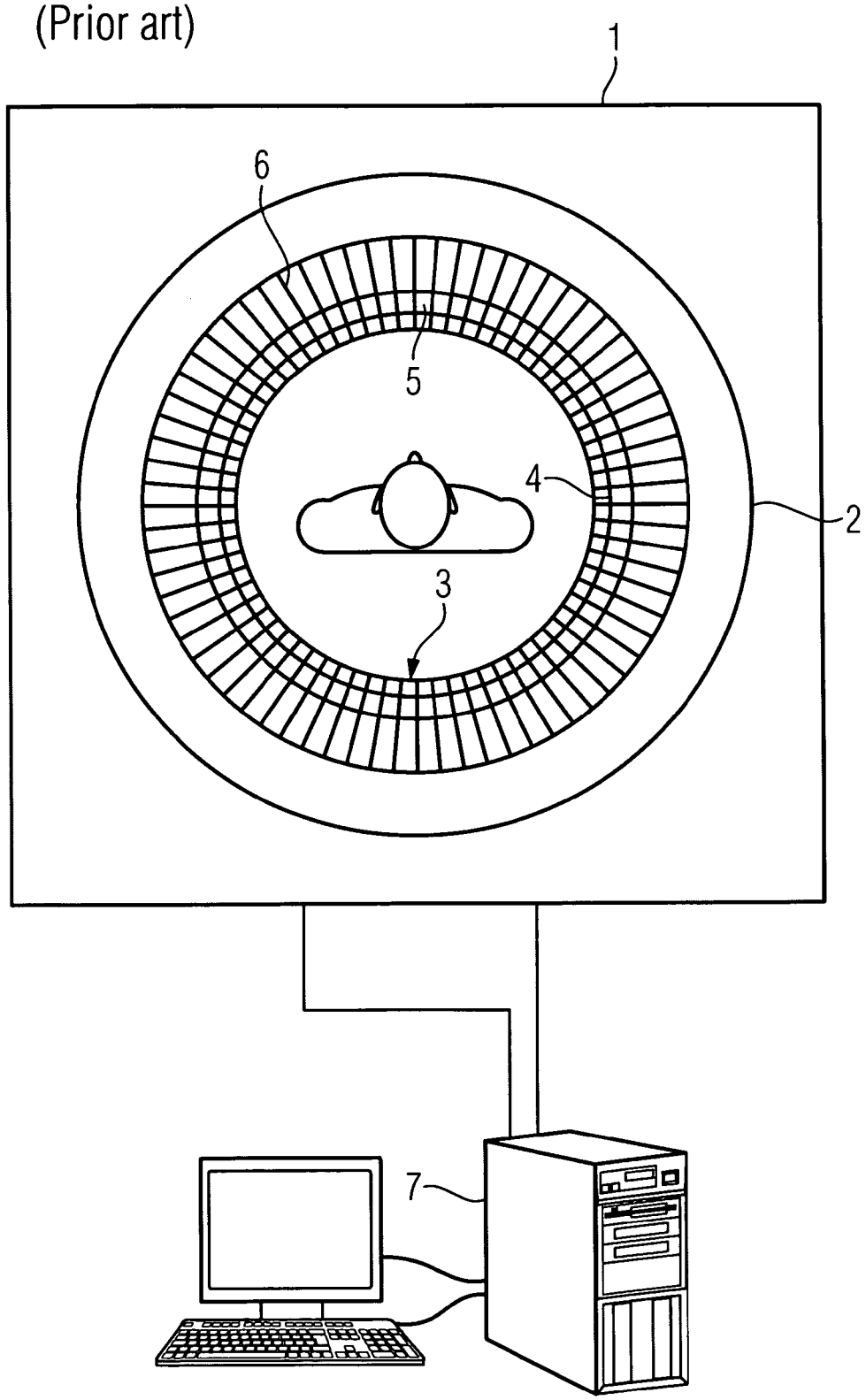
FIG. 1 is a schematic representation of an MR/PET scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used with a combined MR/PET scanner. A combined scanner has the advantage that both MR and PET data can be acquired isocentricaly. This enables the target volume to be precisely defined within the region of interest using the data of the first modality (PET) and this information to be used in the other modality (e.g. magnetic resonance). Although it is possible to transfer the volume information of the region of interest from an external PET scanner to an MR scanner, this entails increased overhead in terms of the registration of the data.

Generally, all data which can be determined by way of magnetic resonance or other imaging methods can be ascertained from the region of interest selected on the PET dataset. For example, instead of the spectroscopy data, fMRI data, diffusion maps, T1- or T2-weighted images or quantitative parameter maps can also be acquired by way of magnetic resonance scans in the region of interest. Equally, computed tomography methods (e.g. perfusion measurement, multi-energy imaging) or X-rays can be used. What is advantageous about the described method in each case is that the region of interest can be narrowed down by means of the PET dataset very selectively to a specifically present pathology of the patient.

In addition, however, it is also possible, through use of a plurality of what are termed tracers, to represent different biological characteristics in the PET dataset and thereby optimize still further the region of interest and the volume defined thereby, or to select a plurality of different target volumes at once, which are then analyzed in subsequent examinations.

FIG. 1 shows a known device 1 for superimposed MR and PET image representation. The device 1 consists of a known MR tube 2. The MR tube 2 defines a longitudinal direction z that extends orthogonally to the drawing plane of FIG. 1.

As shown in FIG. 1, a plurality of PET detection units 3 arranged in opposing pairs about the longitudinal direction z are disposed coaxially inside the MR tube 2. The PET detection units 3 preferably consist of an APD photodiode array 5 preceded by an array of LSO crystals 4 and an electrical amplifier circuit (AMP) 6. However, the invention is not limited to the PET detection units 3 having the APD photodiode array 5 preceded by an array of LSO crystals 4, but other kinds of photodiodes, crystals and devices can equally be used for detection purposes.

Image processing for superimposed MR and PET image representation is performed by a computer 7.

Along its longitudinal direction z, the MR tube 2 defines a cylindrical first field of view. The plurality of PET detection units 3 define, along the longitudinal direction z, a cylindrical second field of view. According to the invention, the second field of view of the PET detection units 3 essentially coincides with the first field of view of the MR tube 2. This is implemented by appropriately adapting the arrangement density of the PET detection units 3 along the longitudinal direction z.

Alternatively, the inventive method and its advantageous embodiments can be used on a combined PET/CT scanner.

The object of the example embodiment of the invention explained in the following is to identify and examine plaques in a vessel. However, embodiments of the invention are fundamentally not restricted hereto, but can also be used for investigating other disease patterns, such as cancer, for example. In general, the advantages of the embodiments of the invention can be used in particular where specific examinations for diseases are to be combined with tomographic data in order to facilitate diagnosis and further investigation.

According to one embodiment of the invention, an angiographic image of a vessel is first generated or, as the case may be, provided.

The following figures schematically show images that were acquired by way of an imaging method according to an example embodiment variant of the invention. Generally these are 3D images, which are represented in the figures simply as sectional images.

Figure 2:
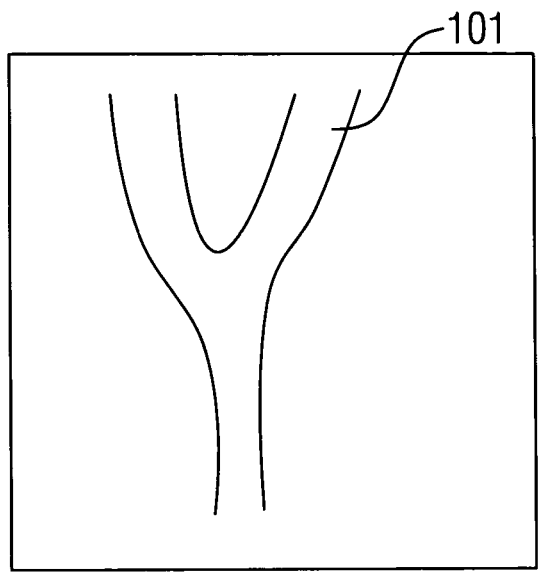
FIG. 2 is a schematic representation of an angiographic image.

FIG. 2 schematically shows an angiographic image of a vessel 101. By way of an embodiment variant of the invention, a search is to be conducted in the vessel 101 for plaques which are then to be specified more closely and investigated. The angiographic image can have been produced according to known methods by way of MR or CT tomography. In the case of MR, a FLASH, TrueFISP or SPACE sequence as well as time-of-flight or phase contrast measurements are used here.

Figure 3:
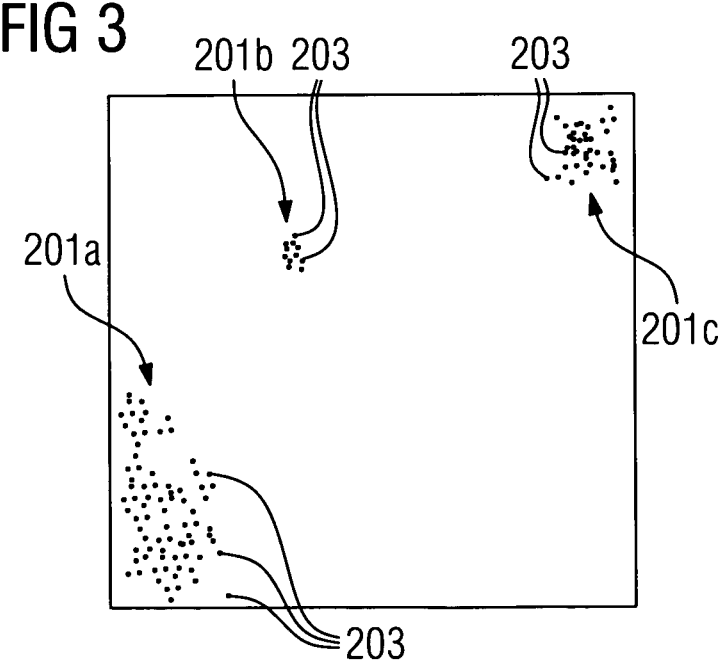
FIG. 3 shows a schematic representation of a PET image.

FIG. 3 shows a recorded PET image of the same region as in FIG. 2. It includes clusters 201*a*, 201*b* and 201*c* of measurement points 203 which in each case stand for the measurement of PET events. For example, the recorded PET image was produced isocentrically with the angiographic image of FIG. 2 using FDG as a tracer. Within the recorded PET image, the clusters 201a, 201b, and 201c, for example, can be identified and localized as hot spots by means of what is termed thresholding. In this case the PET events per cubic millimeter are counted and compared with a threshold value. If the number of events per cubic millimeter exceeds the threshold value, the region is identified as a hot spot. Each of the clusters 201a, 201b and 201c represents a hot spot.

Figure 4:
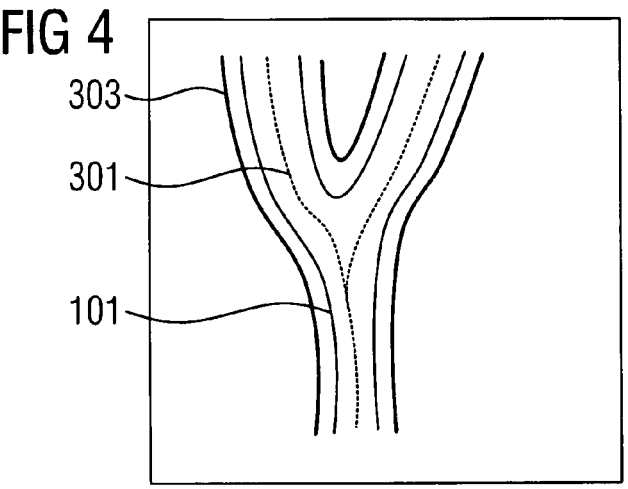
FIG. 4 shows a schematic representation of the segmentation of the angiographic image.

FIG. 4 schematically shows the angiographic image from FIG. 2 after segmentation has been completed. In order to segment the vessel 101 a center line 301 through the vessel 101 is calculated. Around the center line 301 there is placed a tube 303 whose diameter is greater than the maximum diameter of the vessel 101. In this way it is ensured that even if the segmentation is not perfect, the walls of the vessel 101 are recorded in their entirety, and in particular in their full thickness in each case.

Figure 5:
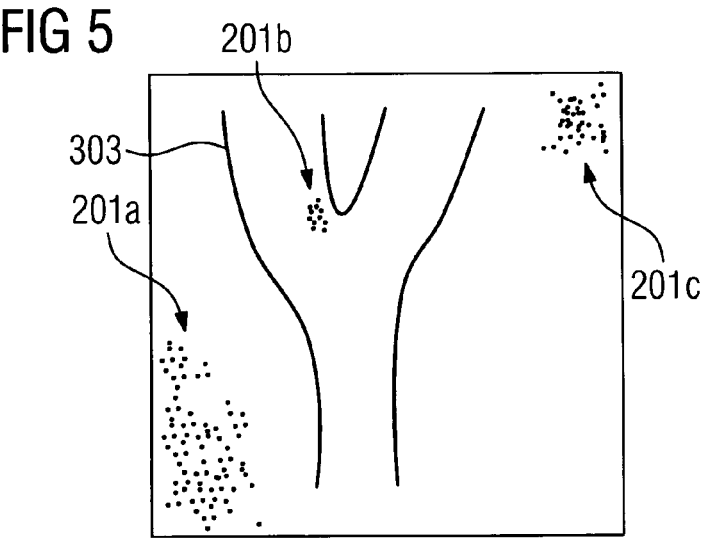
FIG. 5 shows a schematic representation of the transferred segmentation.

FIG. 5 shows a schematic overlay of the recorded PET image from FIG. 2 with the tube 303 from FIG. 4. Accordingly, the segmentation of the vessel 101 from FIG. 4 has been transferred to the recorded PET image from FIG. 2. It is thus easy to recognize that the cluster 201b lies inside the tube 303, while the clusters 201a and 201b lie outside of the tube 303 and consequently cannot be attributed to the vessel 101. With the aid of this representation it is easy for a physician to recognize that the cluster 201b may be a plaque. Accordingly, a localization for a more detailed examination is defined at the center of the cluster 201b.

Figure 6:
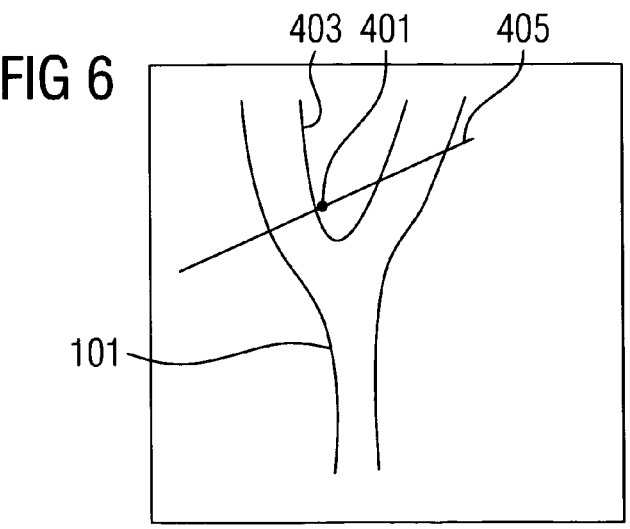
FIG. 6 shows a schematic representation of the angiographic image with a localization for planning a follow-up measurement.

FIG. 6 is once again a schematic representation of the angiographic image from FIG. 2 with the vessel 101. The cluster 201b is represented here as the localization 401. It lies in the vicinity of a wall 403 of the vessel 101. For closer examination of the localization 401 a measurement layer 405 has been defined which is located vertically with respect to the nearby vessel wall 403 and traverses the localization 401. In a subsequent MR examination with the chosen measurement layer 405 the localization 401 can be examined in greater detail and in this way it can be identified exactly whether a plaque is present here. In this case T1, T2 and proton density measurements can be used, for example. The composition of the plaque can also be investigated.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing an imaging examination technique, comprising:
measuring a first dataset via a first imaging examination technique;
measuring a second dataset via a second imaging examination technique;
segmenting the first dataset, the segmenting including, calculating a central line through a center of a vessel, and
specifying at least one region around the central line such that the region contains the vessel, a diameter of the region being greater than a maximum vessel diameter;
transferring the segmentation to the second dataset;
selecting at least one localization in the second dataset based upon the transferred segmentation; and
measuring a third dataset via a third imaging examination technique such that the third dataset includes the selected at least one localization.

2. The method as claimed in claim 1, wherein the first and the second imaging examination techniques are performed on isocentric target volumes and the segmentation is transferred isocentrically between the first and second dataset.

3. The method as claimed in claim 2, wherein the selection of the at least one localization comprises:
identifying regions of interest in the second dataset;
comparing a location of each of the regions of interest with the segmentation;
identifying at least one of the regions of interest that satisfies a location criterion within the segmentation; and
specifying the selected at least one localization as the center of the at least one identified region of interest.

4. The method as claimed in claim 3, wherein the regions of interest are identified via a threshold value comparison.

5. A non-transitory computer readable medium including program segments for, when executed on a computer device, causing the computer device to implement the method of claim 2.

6. The method as claimed in claim 1, wherein target volumes of the first and second imaging examination techniques have isocenters at different locations and the segmentation is transferred between the first and second dataset following a translation of the segmentation such that the two isocenters can be transferred into each other.

7. The method as claimed in claim 6, wherein the selection of the at least one localization comprises:
identifying regions of interest in the second dataset;
comparing a location of each of the regions of interest with the segmentation;
identifying at least one of the regions of interest that satisfies a location criterion within the segmentation; and
specifying the selected at least one localization as the center of the at least one identified region of interest.

8. The method as claimed in claim 7, wherein the regions of interest are identified via a threshold value comparison.

9. The method as claimed in claim 1, wherein the selection of the at least one localization comprises:
identifying regions of interest in the second dataset;
comparing a location of each of the regions of interest with the segmentation;
identifying at least one of the regions of interest that satisfies a location criterion within the segmentation; and
specifying the selected at least one localization as a center of the at least one identified region of interest.

10. The method as claimed in claim 9, wherein the regions of interest are identified via a threshold value comparison.

11. The method as claimed in claim 9, wherein different sections are identified by way of the segmentation within the first dataset.

12. A non-transitory computer readable medium including program segments for, when executed on a computer device, causing the computer device to implement the method of claim 9.

13. The method as claimed in claim 11, wherein the location criterion is an association of the region of interest with a specific one of the sections.

14. The method as claimed in claim 1, wherein the at least one localization is visualized on a display medium together with the first dataset and a user has an option to select one or more localizations for further investigation.

15. The method as claimed in claim 14, wherein following selection of the at least one localization, a list of parameters is generated for performing the third imaging measurement method, by which measurement data is recordable of a layer which contains the selected at least one localization and is oriented perpendicularly with respect to a nearby wall of the vessel.

16. The method as claimed in claim 1, wherein at least one vessel is isolated by way of the segmentation.

17. The method as claimed in claim 1, wherein two regions are specified by way of a boundary line of the region.

18. The method as claimed in claim 1, wherein the first imaging examination technique is MR angiography.

19. The method as claimed in claim 1, wherein the second imaging examination technique is PET.

20. The, method as claimed in claim 1, wherein the third imaging examination technique is MR.

21. A non-transitory computer readable medium including program segments for, when executed on a computer device, causing the computer device to implement the method of claim 1.

22. A method for performing an imaging examination technique, comprising:
measuring a first dataset via a first imaging examination technique;
measuring a second dataset via a second imaging examination technique;
segmenting the first dataset;
transferring the segmentation to the second dataset;
selecting at least one localization in the second dataset based upon the transferred segmentation, the at least one localization being visualized on a display medium together with the first data set and a user having an option to select one or more localizations for further investigation, wherein following the selection of the at least one localization, a list of parameters is generated for performing the third imaging measurement method, by which measurement log measurement data is recordable of a layer which contains the selected at least one localization and is oriented perpendicularly with respect to a nearby portion of the segmented first dataset; and
measuring a third dataset via a third imaging examination technique such that the third dataset includes the selected at least one localization.

* * * * *